United States Patent [19]

Dumoulin

[11] Patent Number: 5,335,660
[45] Date of Patent: Aug. 9, 1994

[54] MAGNETIC RESONANCE METHOD OF MEASURING KIDNEY FILTRATION RATES

[75] Inventor: Charles L. Dumoulin, Ballston Lake, N.Y.

[73] Assignee: General Electric Company, Schenectady, N.Y.

[21] Appl. No.: 105,239

[22] Filed: Aug. 12, 1993

[51] Int. Cl.⁵ ............................................. A61B 5/055
[52] U.S. Cl. ............................... 128/653.3; 128/653.4
[58] Field of Search ................. 128/653.2, 653.3, 653.4

[56] References Cited

U.S. PATENT DOCUMENTS 4,893,627  1/1990  Kehayias et al. ................ 128/653.4

OTHER PUBLICATIONS

Proceedings of the Eleventh Annual Meeting of the Society of Magnetic Resonance in Medicine, by Campeau, et al, p. 434, 1992.
Numerical Recipes in Fortran, The Art of Scientific Computing, William Press, et al, pp. 678–683, 1992.

*Primary Examiner*—Ruth S. Smith
*Attorney, Agent, or Firm*—Lawrence P. Zale; Marvin Snyder

[57] ABSTRACT

A magnetic resonance imaging system employs a sequence of radio frequency pulses and magnetic field gradients to detect and measure the spin-relaxation time of moving blood within a subject. Spin-lattice relaxation times are determined by first inverting longitudinal spin magnetization and then detecting the recovery of this magnetization with a series of detection radio frequency pulses. The inversion pulse is applied to the entire subject, but the detection pulses are applied only to a selection portion of the subject. Blood motion causes the blood in the detection region to be replaced for each detection pulse, thereby increasing the accuracy of the measurement and permitting the use of multiple detection pulses after a single inversion pulse. In-vivo application of this invention can be used to assess renal function in individual kidneys.

4 Claims, 9 Drawing Sheets

MAGNETIC RESONANCE METHOD OF MEASURING KIDNEY FILTRATION RATES

CROSS REFERENCE TO RELATED APPLICATIONS

This application is related to applications "Methods for measurement of Longitudinal Spin Relaxation Times in Moving Liquids" (Ser. No. 08/185,256), "Methods for High Speed Measurement of Spin-Lattice Relaxation Times" (Ser. No. 08/105,249) both by Charles L. Dumoulin, filed concurrently with this application, and assigned to the present assignee.

BACKGROUND OF THE INVENTION

1. Field of the Invention

The present invention relates to the fields of nuclear magnetic resonance spectroscopy and magnetic resonance (MR) imaging, and more specifically longitudinal spin relaxation time measurement, and the in-vivo assessment of renal function.

2. Discussion of Prior Art

Presently, the measurement of in-vivo spin-lattice relaxation times is a useful procedure in diagnostic radiology. In these procedures a subject is placed in a magnet to generate longitudinal spin magnetization in resonating nuclei of the subject or "nuclear spins". In the most commonly used procedure (known as Inversion Recovery) this magnetization is inverted by the application of a radio frequency pulse capable of nutating the longitudinal spin magnetization 180°. When the magnetization of the subject's nuclear spins is inverted, it spontaneously returns to the non-inverted equilibrium state. The return to the equilibrium state occurs in an exponential fashion having a half-life which is characteristic of the molecular environment of the nuclear spin. This half-life is frequently given the name longitudinal spin relaxation time, $T_1$.

During the return to the equilibrium (or fully relaxed) state, the longitudinal magnetization cannot be directly detected. The instantaneous mount of longitudinal magnetization can be measured, however, by applying a sampling RF pulse. This sampling RF pulse nutates the longitudinal magnetization into the transverse plane, thereby creating transverse spin magnetization. Maximum transverse spin magnetization is generated by the application of a 90° nutation. Unlike longitudinal magnetization, transverse spin magnetization is capable of inducing a signal in a receiver coil placed near the subject. Once transverse spin magnetization is generated, it can be phase shifted using magnetic field gradient pulses of selected intensities and durations. These gradient-induced phase shifts encode the position of spin magnetization within the magnet. Two or three-dimensional images of the distribution of spin magnetization can be generated by repeating the sequence of RF and magnetic field gradient pulses and acquiring the MR signal responsive to a collection of magnetic field gradient intensities.

In-vivo measurement of $T_1$ with previously available methods typically requires a long acquisition time. This is because the longitudinal magnetization must be measured at multiple points in time after the inversion pulse to accurately determine the half-life of the recovery. Only a single sampling pulse can be used during the recovery process. This is because application of a sampling pulse disturbs the longitudinal spin magnetization, and thus compromises the integrity of measurements generated by any subsequent sampling pulses. Furthermore, best results are obtained when full recovery of longitudinal spin magnetization occurs after each sampling pulse. For in-vivo applications the time for full relaxation is between 1500 and 5000 ms, since most in-vivo $T_1$ values are between 300 and 1000 ms. Measurement of $T_1$ for each pixel in an image may require exam times as long as an hour, since enough data must be acquired to construct an image (typically with a resolution of 256×256), for each of several sampling times (typically 4–8) after each inversion pulse.

An alternative method for in-vivo $T_1$ measurement described by Campeau et. al. in the Proceedings of the Eleventh Annual Meeting of the Society of Magnetic Resonance in Medicine, 1992, pg. 434, employs a series of slice selective inversion pulses which excite slices placed orthogonal to the image plane of an acquired MR image. Each inverted slice is in a unique location and each inversion pulse is applied at a unique time before the application of the transverse spin magnetization generation pulse of the imaging pulse sequence. If the acquired image has relatively large features of homogeneous $T_1$, (e.g. a large skeletal muscle) the resulting image will contain a series of stripes, each created by spin inversion at selected times prior to the application of the detection pulse. The $T_1$ values of the selected image feature can then be determined by measuring the pixel intensity in each stripe corresponding to each inversion delay time and fitting the result to an exponential equation to determine the rate constant, $T_1$. While this method is relatively fast, it is not suited for the $T_1$ measurement of small features such as the blood in a selected blood vessel. The technique is also poorly suited for $T_1$ measurement of moving blood, since blood motion during the period between each selective inversion pulse and the detection pulse causes mixing of the inverted boluses of blood.

Present clinical techniques used to assess renal function are based on the concept of clearance. Under normal steady-state conditions, the daily production of creatinine is equal to its daily excretion, thereby regulating serum creatinine within a narrow range. Thus, clinicians frequently use serum creatinine concentration alone as an estimate of the Glomerular Filtration Rate (GFR). This technique, however, has limited accuracy and the presence of unilateral kidney disease is usually not detectable. Since this test may detect a normal serum creatinine concentration even in the presence of a 50% reduction in GFR, renal insufficiency may be misdiagnosed.

Currently there is a need for a non-invasive method of measuring the longitudinal spin relaxation time of moving liquids for use in application such as in assessing renal function.

OBJECTS OF THE INVENTION

An object of the present invention is to provide a system which is capable of rapid longitudinal spin relaxation time, $T_1$, measurements.

Another object of the present invention is to provide a system which measures the $T_1$ of blood in selected blood vessels.

Another object of the present invention is to provide a method in which blood velocity measurements are made of a volume of moving blood simultaneously with $T_1$ measurements of the same blood volume.

Another object of the present invention is to provide a method in which $T_1$ measurements of moving blood are employed in assessing renal function.

SUMMARY OF THE INVENTION

In the present invention, a subject is placed in a Magnetic Resonance Imaging (MRI) system. A novel inversion recovery MR pulse sequence is then used to measure the $T_1$ of moving blood. This pulse sequence employs an inversion pulse which is not spatially selective to invert all nuclear spins within a selected portion of the subject. The inversion pulse is followed by a series of detection pulses which nutate the longitudinal magnetization by as much as 90 degrees. These detection pulses are spatially selective and in the present invention have a slice profile. Each detection pulse is applied in the same location in the subject. This location is chosen to transect a selected blood vessel in which blood is flowing. Since all the blood in the subject exhibits inverted longitudinal spin magnetization and since blood motion replaces blood in the detection slice after each detection pulse, longitudinal spin magnetization is accurately sampled. In addition, sampling of longitudinal spin magnetization is performed a plurality, N, times during the recovery process, instead of once as in prior methods. This results in an N-fold reduction in the total scan time.

In one embodiment of the present invention velocity-encoding magnetic field gradient pulses are incorporated into the pulse sequence to permit the measurement of blood velocity simultaneously with the measurement of blood $T_1$.

The novel pulse sequence of the present invention can be used for the assessment of single kidney hemodynamic function. For example, after injection of an MR contrast agent such as Gadolinium diethylene triamine pentaacetic acid (Gd-DTPA) into the subject, the agent is excreted through the subject's kidneys. The efficiency of renal filtration of the contrast agent, or Filtration Fraction (FF), can be derived by measuring the $T_1$ of blood in the arterial system (before it passes through the kidney) and the renal vein. When the filtration fraction measurement is combined with blood velocity measurements in the renal vessels, the Glomerular Filtration Rate (GFR) can be determined.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

DETAILED DESCRIPTION OF THE INVENTION

In the present embodiment of the invention, a subject is placed within the magnet of a magnetic resonance imaging system. The region over which longitudinal spin relaxation time, $T_1$, measurement is desired is then identified by an operator, perhaps with the assistance of a conventional MR imaging sequence. A pulse sequence is then applied and the data analyzed.

Figure 1:
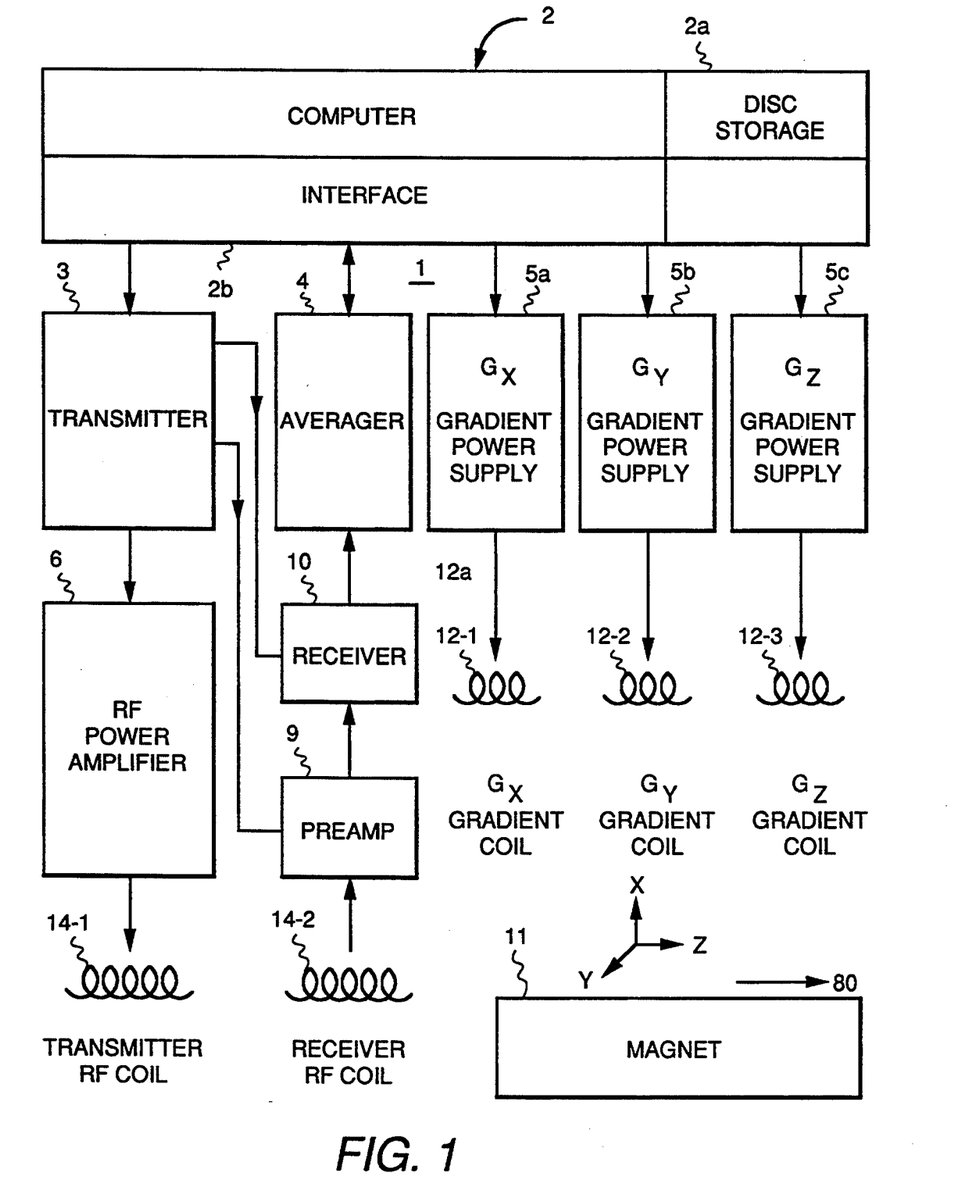
FIG. 1 is a simplified block diagram of a magnetic resonance (MR) imaging system suitable for use with the present invention.

FIG. 1 is a simplified block diagram of the major components of a magnetic resonance (MR) imaging system suitable for use with the invention described herein. The system is made up of a general purpose mini-computer 2 which is functionally coupled to a disk storage unit 2a and an interface unit 2b. A radiofrequency (RF) transmitter 3, signal averager 4, and gradient power supplies 5a, 5b and 5c, are all coupled to computer 2 through interface unit 2b. Gradient power supplies 5a, 5b, 5c energize gradient coils 12-1, 12-2, 12-3 to create magnetic field gradients $G_x$, $G_y$, $G_z$, respectively, in the "X", "Y", "Z" directions, respectively, over a subject to be imaged. RF transmitter 3 is gated with pulse envelopes from computer 2 to generate RF pulses having the required modulation to excite an MR response signal from a subject. The RF pules are amplified in an RF power amplifier 6 to levels varying from 100 watts to several kilowatts, depending on the imaging method, and applied to a transmitter coil 14-1. The higher power levels are necessary for large sample volumes, such as in whole body imaging, and where short duration pulses are required to excite larger NMR frequency bandwidths.

The MR response signal is sensed by a receiver coil 14-2, amplified in a low noise preamplifier 9 and passed to receiver 10 for further amplification, detection, and filtering. The signal is then digitized for averaging by signal averager 4 and for processing by computer 2. Preamplifier 9 and receiver 10 are protected from the RF pulses during transmission by active gating or by passive filtering.

Computer 2 provides gating and envelope modulation for the MR pulses, blanking for the preamplifier and RF power amplifier, and voltage waveforms for the gradient power supplies. The computer also performs data processing such as Fourier transformation, image reconstruction, data filtering, imaging display, and storage functions (all of which are conventional and outside the scope of the present invention).

Transmitter coil 14-1 and receiver RF coil 14-2, if desired, may comprise a single coil. Alternatively, two separate coils that are electrically orthogonal may be used. The latter configuration has the advantage of reduced RF pulse breakthrough into the receiver during pulse transmission. In both cases, the coils are orthogonal to the direction of a static magnetic field $B_0$ produced by a magnet means 11. The coils may be isolated from the remainder of the system by enclosure in an RF shielded cage.

Magnetic field gradient coils 12-1, 12-2, and 12-3 are necessary to provide gradients $G_x$, $G_y$, and $G_z$, respectively, that are monotonic and linear over the sample volume. Multivalued gradient fields cause a degradation in the MR response signal data, known as aliasing, which leads to severe image artifacts. Nonlinear gradients cause geometric distortions of the image.

Figure 2:
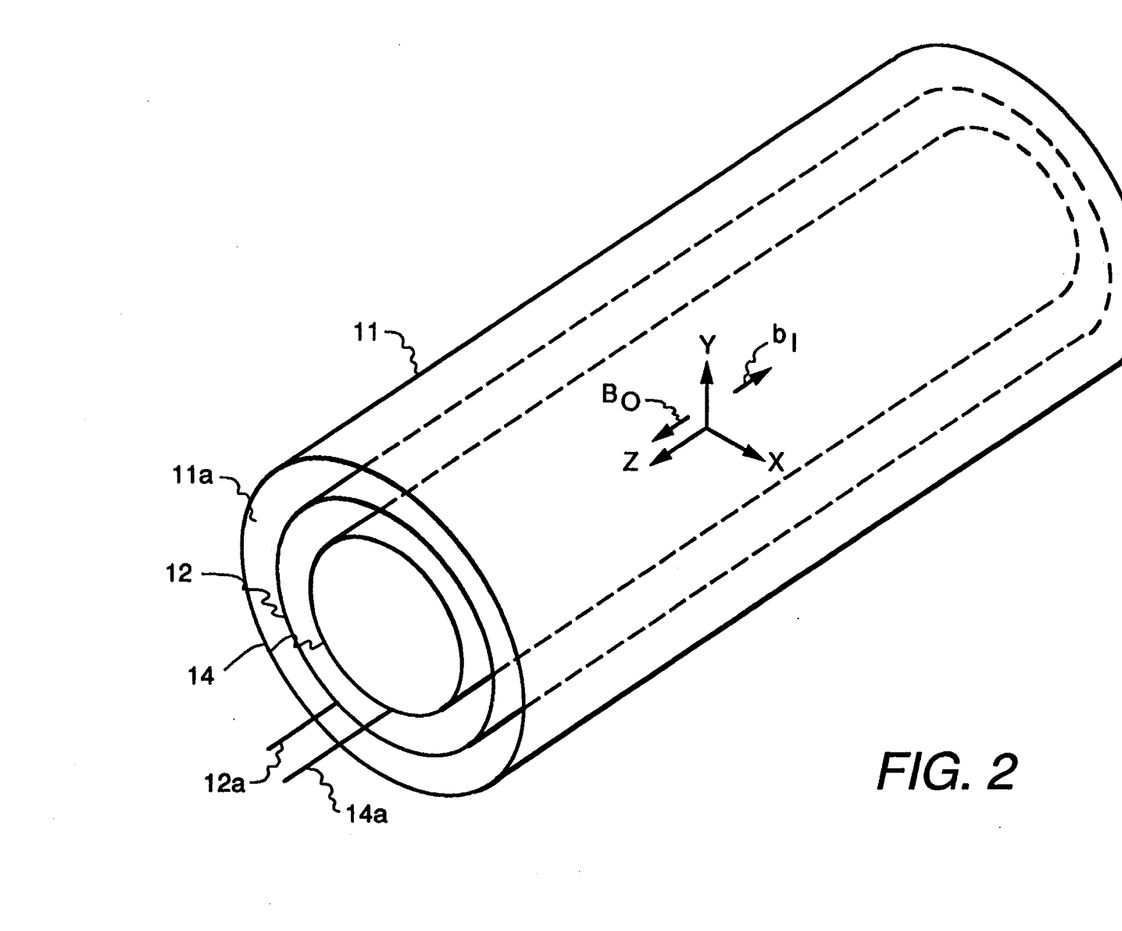
FIG. 2 is a more detailed diagram of the magnet assembly of FIG. 1.

Magnet assembly 11, shown schematically in FIG. 2, has a central cylindrical bore 11a which generates a static magnetic field $B_0$, typically in the axial, or Z Cartesian coordinate direction. A set of coils 12, such as coils 12-1, 12-2, 12-3 of FIG. 1, receive electrical signals via input connections 12a, and provide at least one gradient magnetic field within the volume of bore 11a. Also situated within bore 11a is an RF coil 14, which receives RF energy via at least one input cable 14a, to provide an RF magnetic field $b_1$, typically in the X-Y plane.

Figure 3:
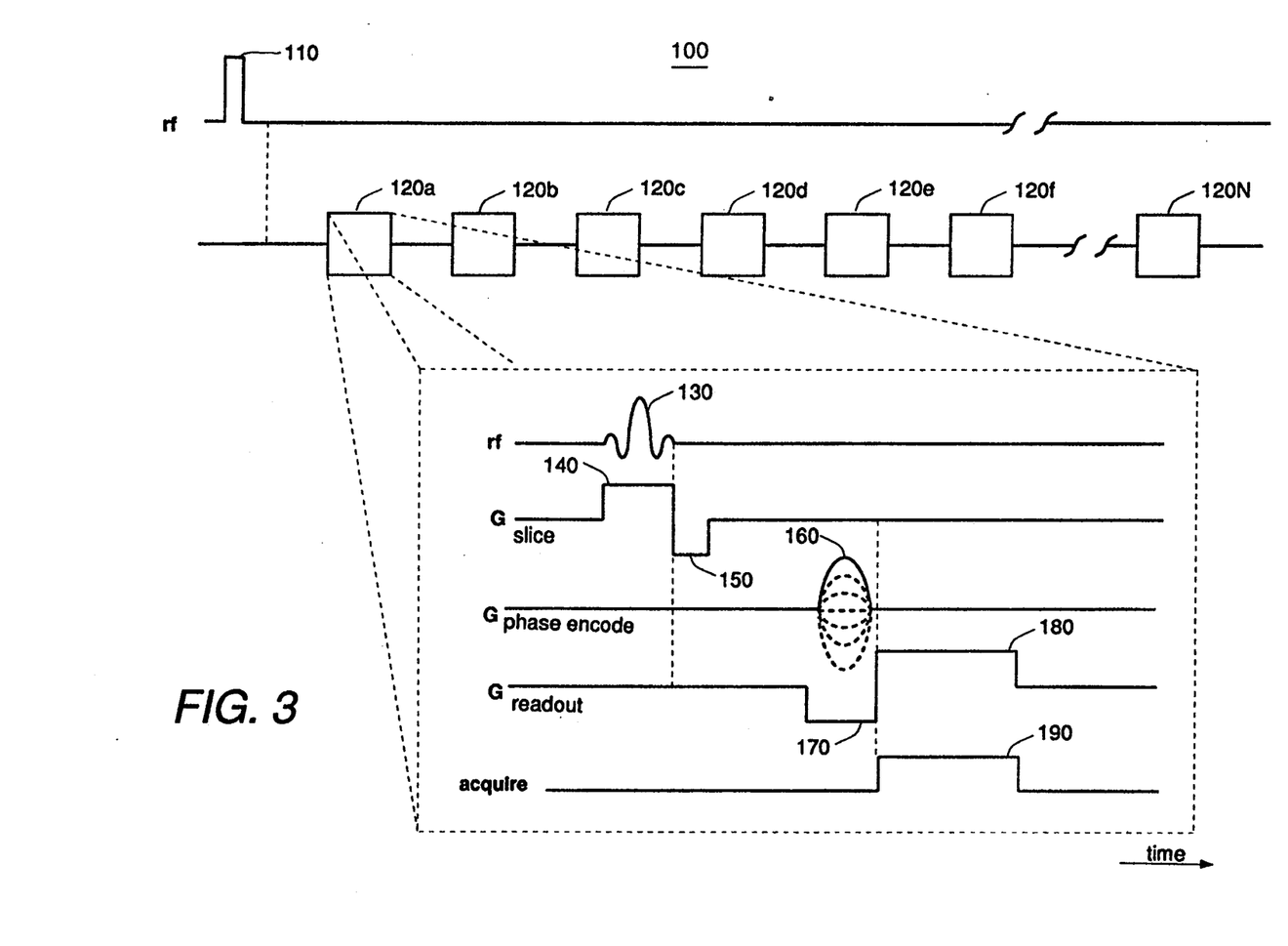
FIG. 3 is a pulse sequence diagram of a first embodiment of the present invention which can be used to measure the longitudinal spin relaxation time, $T_1$, of moving blood.

FIG. 3 is a pulse sequence diagram of radio frequency (RF) pulses and magnetic field gradients employed in a first embodiment of the present invention which may be executed by the MR imaging system of FIGS. 1 and 2. Pulse sequence 100 consists of a non-selective inversion radio frequency (RF) pulse 110 which substantially inverts all spin magnetization within the excitation radio frequency coil of the imaging system. In the present embodiment of the invention inversion RF pulse 110 is applied without the simultaneous application of a magnetic field gradient pulse. If it is desirable to restrict the volume of inversion, a magnetic field gradient pulse can be applied simultaneously with an inversion pulse in a manner well known to those skilled in the art.

At a selected time after inversion RF pulse 110 is applied, a first subsequence 120a is applied. Subsequence 120a is comprised of a detection RF pulse 130 which is applied in the presence of a slice selective magnetic field gradient pulse 140. Detection pulse 130 nutates spin magnetization in a selected portion of the subject. The amount of nutation can be selected by selecting the duration and amplitude of detection pulse 130. Maximum transverse magnetization is most often obtained with a nutation angle of 90 degrees. The location and size of the selected portion can be adjusted by appropriate selection of the frequency and bandwidth of RF pulse 130 and the amplitude of slice selective magnetic field gradient pulse 140. In the present embodiment of the invention the selected portion has a planar geometry of selected thickness. In alternative embodiments, a non-planar geometry such as a cylinder, can be used as described in U.S. Pat. No. 5,133,357 "Quantitative Measurement of Blood Flow Using Cylindrically Localized Fourier Velocity Encoding" issued Jul. 28, 1992, assigned to the present assignee, and hereby incorporated by reference.

After the detection RF pulse 130 and slice selective magnetic field gradient pulse 140 are applied, a slice refocusing magnetic field gradient pulse 150 is applied. Slice refocusing gradient pulse 150 has an amplitude and duration which is selected to cause all transverse spin magnetization within the selected portion of the subject to be substantially in phase after the application of slice refocusing gradient pulse 140. In the present embodiment the product of the amplitude and duration of slice refocusing gradient pulse 150 is substantially half that of the negative of the product of the amplitude and duration of slice selective gradient pulse 140 in a manner well known to those skilled in the art.

After detection RF pulse 130 and slice selective gradient pulse 140 have been applied, a phase encoding magnetic field gradient pulse 160 of a selected amplitude is applied. Phase encoding gradient pulse 160 is applied in a direction substantially orthogonal to slice selective gradient pulse 140 and can be applied simultaneously with slice refocusing pulse 150 if desired. For the sake of clarity, phase encoding pulse 160 and slice refocusing pulse 150 are not shown to be simultaneous in FIG. 3, but it is possible to apply both simultaneously.

After detection RF pulse 130 and slice selective gradient pulse 140 have been applied, a readout dephasing magnetic field gradient pulse 170 of a selected amplitude is applied. Readout dephasing gradient pulse 170 is applied in a direction substantially orthogonal to both slice selective gradient pulse 140 and phase encoding pulse 160. Readout dephasing pulse 170 can be applied simultaneously with either slice refocusing pulse 150 or phase encoding pulse 160 if desired. Readout dephasing pulse 170 causes transverse magnetization at different positions along the direction of the readout dephasing magnetic field gradient to obtain phase shifts which are proportional to position in the readout direction.

Following the application of slice refocusing pulse 150, phase encoding pulse 160 and readout dephasing pulse 170, a readout magnetic field gradient pulse 180 is applied. Readout pulse 180 is applied in the same direction as readout dephasing pulse 170, but is given the opposite polarity. The amplitude and duration of readout pulse 180 is selected so that substantially all transverse spin magnetization has an identical phase shift at a selected point during readout pulse 180.

Substantially simultaneously with readout pulse 180, a data acquire signal pulse 190 is sent to a data acquisition subsystem which is part of the imaging system. MR signals are digitized during data acquire pulse 190. Since the MR signals coming from transverse spin magnetization within the selected portion of the subject are acquired during readout magnetic field gradient 180, each detected MR signal will have a frequency which is proportional to the location of the position of the transverse spin magnetization which generated said signal. The location of each signal source can be determined by applying a Fourier transformation to the acquired signal data in a fashion well known to those skilled in the art.

At a selected time interval after the application of subsequence 120a, a second subsequence 120b is applied. Subsequence 120b is substantially identical to subsequence 120a. Data acquired responsive to subsequence 120b, however, is stored in its own location. Subsequence 120b is followed after a selected interval by a third subsequence 120c and so on until a plurality, N, subsequences have been applied. In the embodiment of the invention illustrated in FIG. 3 the interval between each subsequences is the same. In alternative embodiments the intervals can be arbitrarily chosen by the operator.

Pulse sequence 100 is repeated a plurality, Y, times. In each repetition of pulse sequence 100, phase encoding pulse 160 is given a different amplitude. For each repetition of pulse sequence 100, however, the amplitude of phase encoding pulse 160 is identical for each subsequence 120a–120N. Phase encoding pulse 160 causes phase shifts in the detected MR signals which are proportional to the position of transverse spin magnetization along the direction of phase encoding magnetic field gradient 160. Data acquired responsive to different amplitudes of phase encoding gradient 160 can be Fourier transformed to give the position (in the direction of phase encoding gradient 160) of the signal producing transverse spin magnetization in a manner well known to those skilled in the art.

Once data has been collected responsive to Y repetitions of N subsequences, a total of N magnetic resonance images can be constructed. These N images will have pixels whose intensifies vary as a function of a time interval, t, between inversion RF pulse 110 and detection RF pulse 130 of each respective subsequence. The signal intensity, I, for a pixel having a single recovery rate, $T_1$, can be described by the equation:

$$I = A + B^* \exp(-t/T_1) \quad [1]$$

where A and B are constants. $T_1$, A and B of any desired pixel or collection of pixels can be determined by fitting equation 1 to the intensities of the pixel obtained in each of the subsequences. This can be done using a non-linear least square optimization procedure such as that described in "Numerical Recipes in FORTRAN" by W. H. Press, S. A. Teukolsky, W. T. Vetterling and B. P. Flannery, pp. 678–683.

Note that for portions of the subject which are relatively stationary, detection RF pulse 130 is repeatedly applied after inversion RF pulse 110. This causes the intensity of the detected MR signal for stationary tissue to have complicated characteristics which prevent an accurate analysis of $T_1$. Blood contained within arteries and veins of the subject is in motion, however, and as it passes through the detection region, it is subjected only to non-selective inversion RF pulse 110 and a single detection RF pulse 130. For this to happen the blood must be moving at a velocity, V, which is greater than D/T where D is the thickness of the detection region and T is the time interval between detection pulses.

Figure 4:
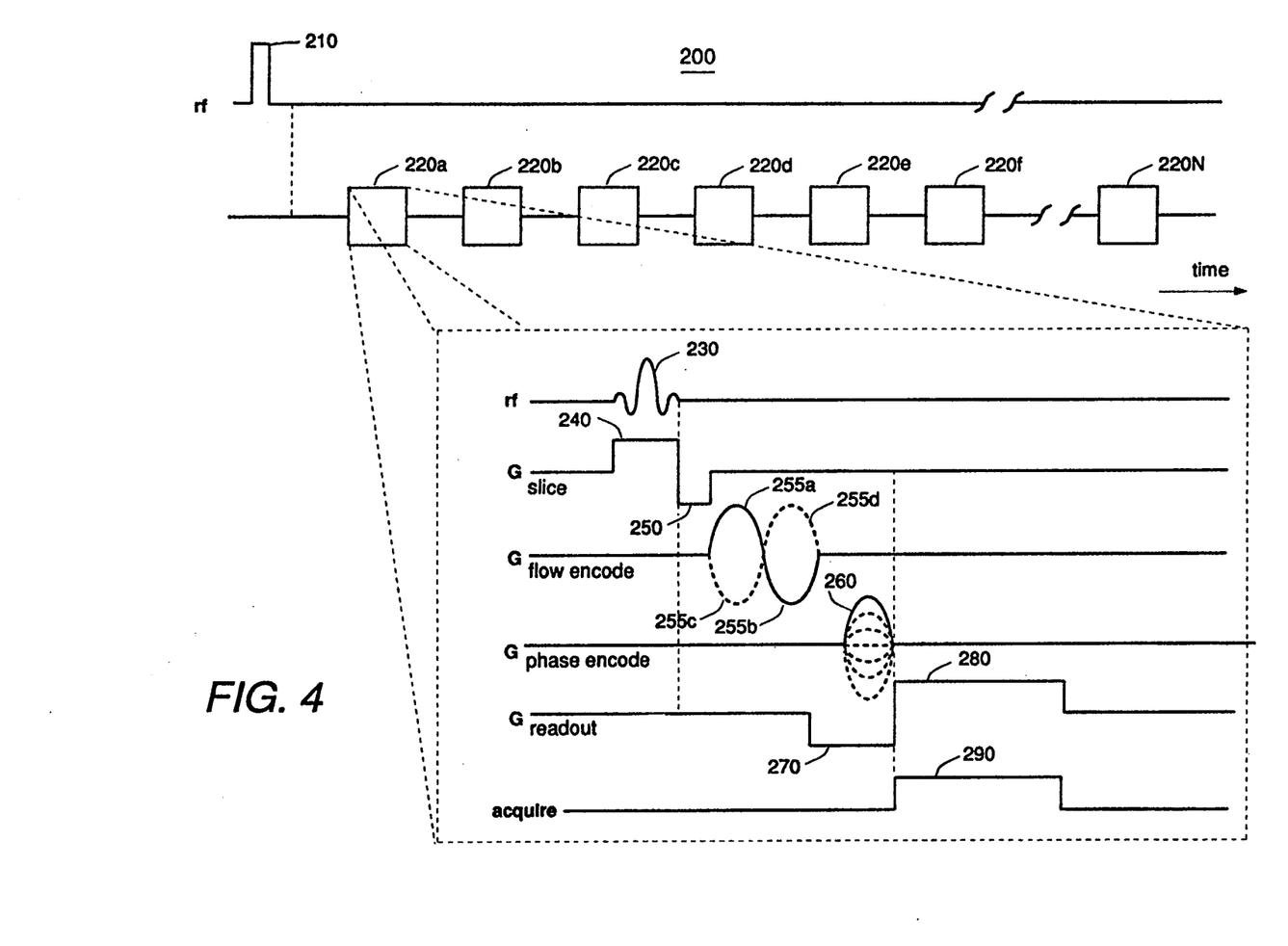
FIG. 4 is a pulse sequence diagram of a second embodiment of the present invention which can be used to simultaneously measure the $T_1$ and velocity of moving blood.

FIG. 4 illustrates a second embodiment of the present invention. Like the embodiment described above in FIG. 3, pulse sequence 200 of FIG. 4 has an inversion RF pulse 210 followed by a plurality, N, of subsequences 220a–200N, Each pulse sequence is further comprised of a detection RF pulse 230, a slice select magnetic field gradient pulse 240, slice refocusing magnetic field gradient pulse 250, a phase encoding magnetic field gradient pulse 260, a readout dephasing magnetic field gradient pulse 270, a readout magnetic field gradient pulse 280 and a data acquire signal pulse 290.

In addition to the RF and magnetic field gradient pulses found in the first embodiment of the present invention, each subsequence 220a–220N in the second embodiment also has a two-lobed flow-encoding magnetic field gradient pulse. The flow-encoding pulse consists of a first flow-encoding magnetic field gradient pulse lobe 255a and a second flow-encoding magnetic field gradient pulse lobe 255b. The product of the pulse duration and amplitude of second flow-encoding pulse lobe 255b is substantially equal to the negative of the product of the pulse duration and amplitude of first flow-encoding pulse lobe 255a.

Successive application of first flow-encoding pulse lobe 255a and second flow-encoding pulse lobe 255b to transverse spin magnetization causes a phase shift in the magnetization which is proportional to the velocity component of the magnetization parallel to the direction of the flow-encoding magnetic field gradient. This phase shift can be used to distinguish moving from stationary transverse spin magnetization. The phase of each portion of transverse spin magnetization, however, will have contributions from sources other than velocity. These sources may include transmitter offsets, chemical shift effects and eddy currents.

In order to remove contributions from all components other than velocity, pulse sequence 200 is repeated and a second data set acquired. The RF and magnetic field gradient pulses of the repeated pulse sequence are identical to that of the first with the exception of first flow-encoding pulse lobe 255a and second flow-encoding pulse lobe 255b. In their place a third flow-encoding pulse lobe 255c followed by a fourth flow-encoding pulse lobe 255d applied. Third and fourth flow-encoding pulse lobes 255c, 255d are identical to first and second flow-encoding 255a, 255b respectively, except that they have opposite polarity. Phase shifts induced by the third and fourth flow-encoding gradient lobes will also have opposite polarity relative to each other. Consequently, when the phase of data acquired responsive to the first application of pulse sequence 200, is subtracted from the phase of the data acquired responsive to the repeated application of pulse sequence 200, phase contributions from all non-velocity sources are substantially canceled, leaving only a phase shift arising from velocity. This phase shift is directly proportional to velocity and can be used to quantify velocity. Note that MR images generated with pulse sequence 200 have velocity information encoded as phase and $T_1$ information encoded as magnitude.

Figure 5:
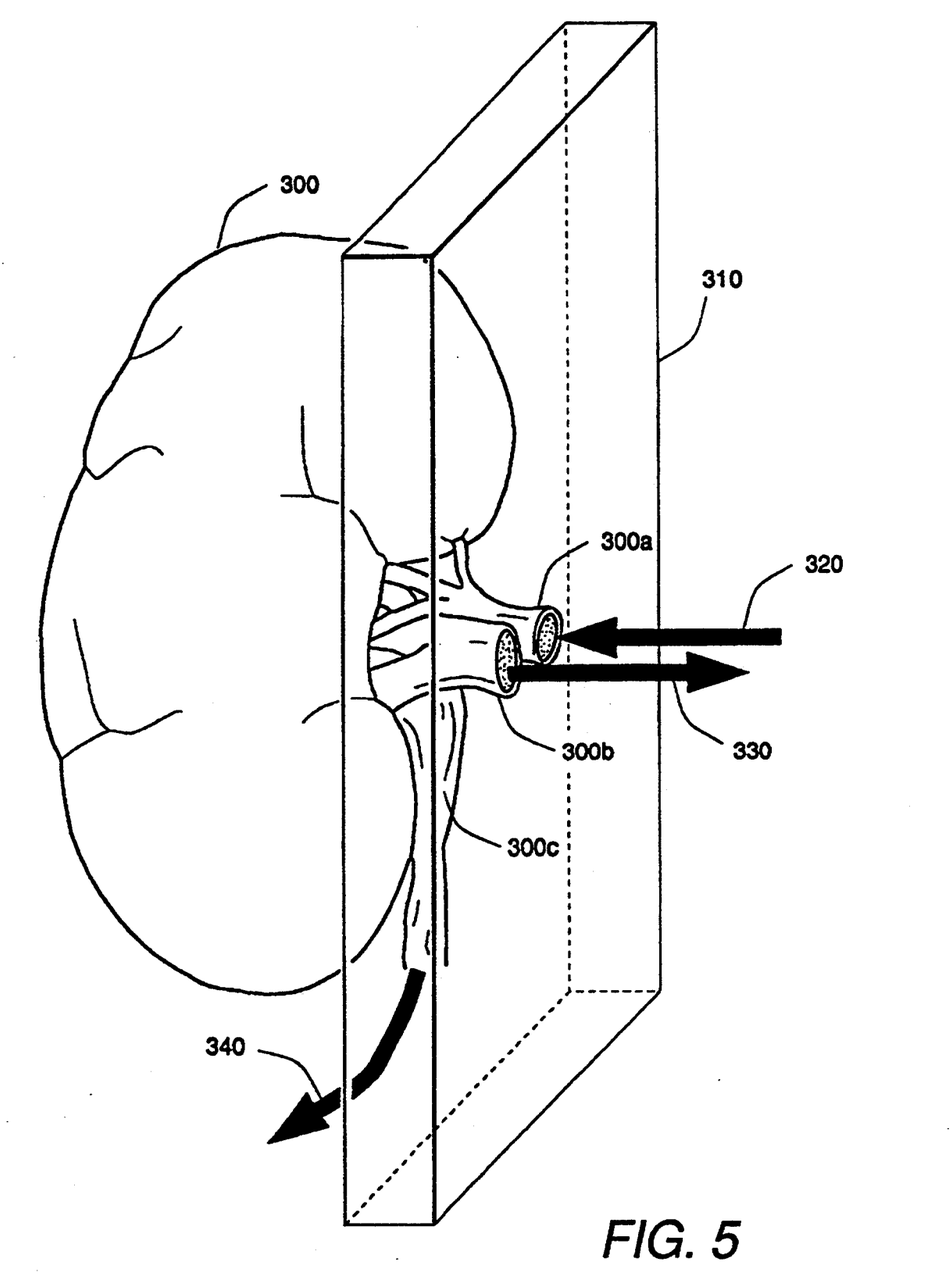
FIG. 5 is an illustration of the scan-plane geometry resulting from pulse sequences of the present invention.

The present invention can be used to evaluate renal function in living systems as illustrated in FIG. 5. In FIG. 5, a kidney 300 present within a living subject is perfused with arterial blood 320 which flows into a renal artery 300a. Kidney 300 removes substances from the blood, and returns venous blood 330 to the body through a renal vein 300b. Substances which are removed from arterial blood 320 are passed through a ureter 300c to the bladder as urine 340. The present invention can be used to assess renal efficiency by measuring the concentration of substances within the subject's bloodstream before it enters, and after it exits the kidney, being prefiltered, and post filtered blood. This is easily done by selection of a suitable slice selection magnetic field gradient 140 and detection RF pulse 130 of FIG. 3 to form an image plane 310. If desired, the present invention can be performed with multiple image planes to concurrently obtain diagnostic information from more than a single location. This may be particularly useful in making independent assessments of renal function in two kidneys.

To evaluate glomerular filtration rates, both the filtering efficiency of the kidney and the blood flow through the kidney must be determined. The filtration fraction, FF, can be determined with the present invention by introducing a longitudinal spin relaxation contrast agent into the bloodstream of the subject. Filtration Fraction can be expressed as:

$$FF = \frac{C_a - C_v}{C_a} \quad [2]$$

where $C_a$ is the concentration of the $T_1$ relaxation contrast agent in the arterial blood entering the kidney and $C_v$ is the concentration of the relaxation contrast agent in the venous blood as it leaves the kidney.

Figure 6:
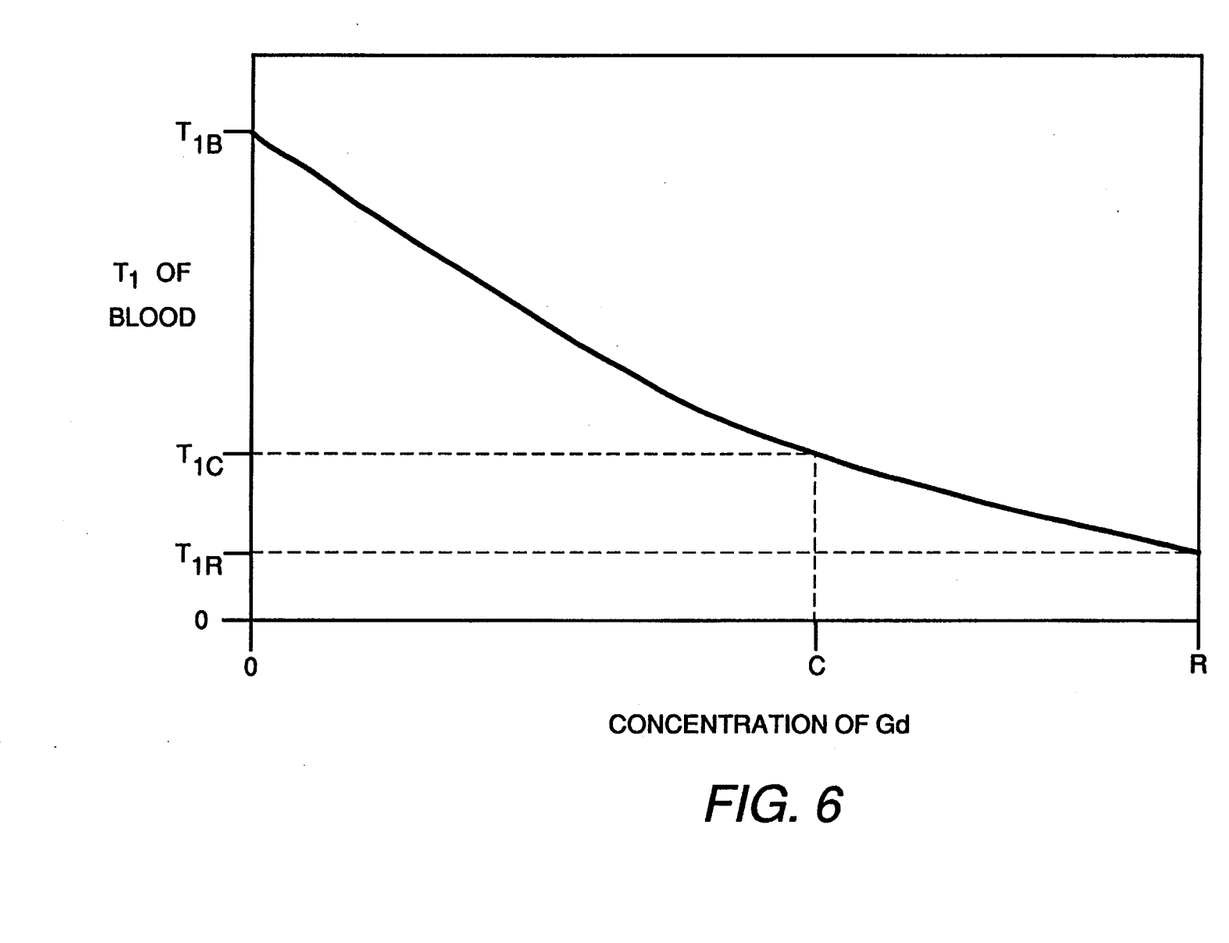
FIG. 6 is a diagram illustrating the relationship between the $T_1$ of blood and the concentration of a longitudinal spin relaxation contrast agent such as Gd-DTPA.

Gadolinium diethylene triamine pentaacetic acid (Gd-DTPA) is a commonly used relaxation contrast agent which is excreted primarily by glomerular filtration in the kidneys. Gd-DTPA, and other $T_1$ relaxation contrast agents, shorten the measured $T_1$ of blood by an amount which is substantially inversely proportional to the concentration of the $T_1$ relaxation contrast agent as illustrated in FIG. 6. In FIG. 6, the $T_1$ of blood in the absence of any $T_1$ relaxation contrast agent (i.e. concentration $=0$) is denoted as $T_{1B}$. At a concentration, C, the $T_1$ relaxation contrast agent reduces the $T_1$ value of blood to $T_{1C}$. Blood having a reference concentration of $T_1$ relaxation contrast agent, R, will have a relaxation time of $T_{1R}$. The observed relaxation time of blood, $T_1$ (observed) for a given concentration, C, of $T_1$ relaxation contrast agent can be expresses as:

$$\frac{1}{T_1(\text{observed})} = \frac{1}{T_{1B}} + \frac{C}{R * T_{1R}} \quad [3]$$

This equation can be rearranged to give:

$$C = \frac{R * T_{1R}}{T_1(\text{observed})} - \frac{R * T_{1R}}{T_{1B}} \quad [4]$$

Equation [4] can be combined with equation [2] if $C_A$ is derived from the observed $T_1$ of the arterial blood and $C_V$ is derived from the observed $T_1$ of the venous blood. The resulting expression for filtration fraction becomes:

$$FF = \frac{T_{1V} - T_{1A}}{T_{1B} - T_{1A}} * \left[ \frac{T_{1V}}{T_{1B}} \right] \quad [5]$$

where $T_{1V}$ is the observed $T_1$ of venous renal blood and $T_{1A}$ is the observed $T_1$ of arterial renal blood.

The accuracy of the measurement of filtration fraction depends on the accuracy of the $T_1$ measurement and on the magnitude of the difference between $T_{1A}$ and $T_{1B}$. Higher concentrations of $T_1$ relaxation contrast agent in the arterial blood will result in a greater reduction in the $T_1$ of blood thereby increasing the denominator of equation [5]. This effect manifests itself as an increase in the dynamic range of FF as illustrated in FIG. 7.

Figure 7:
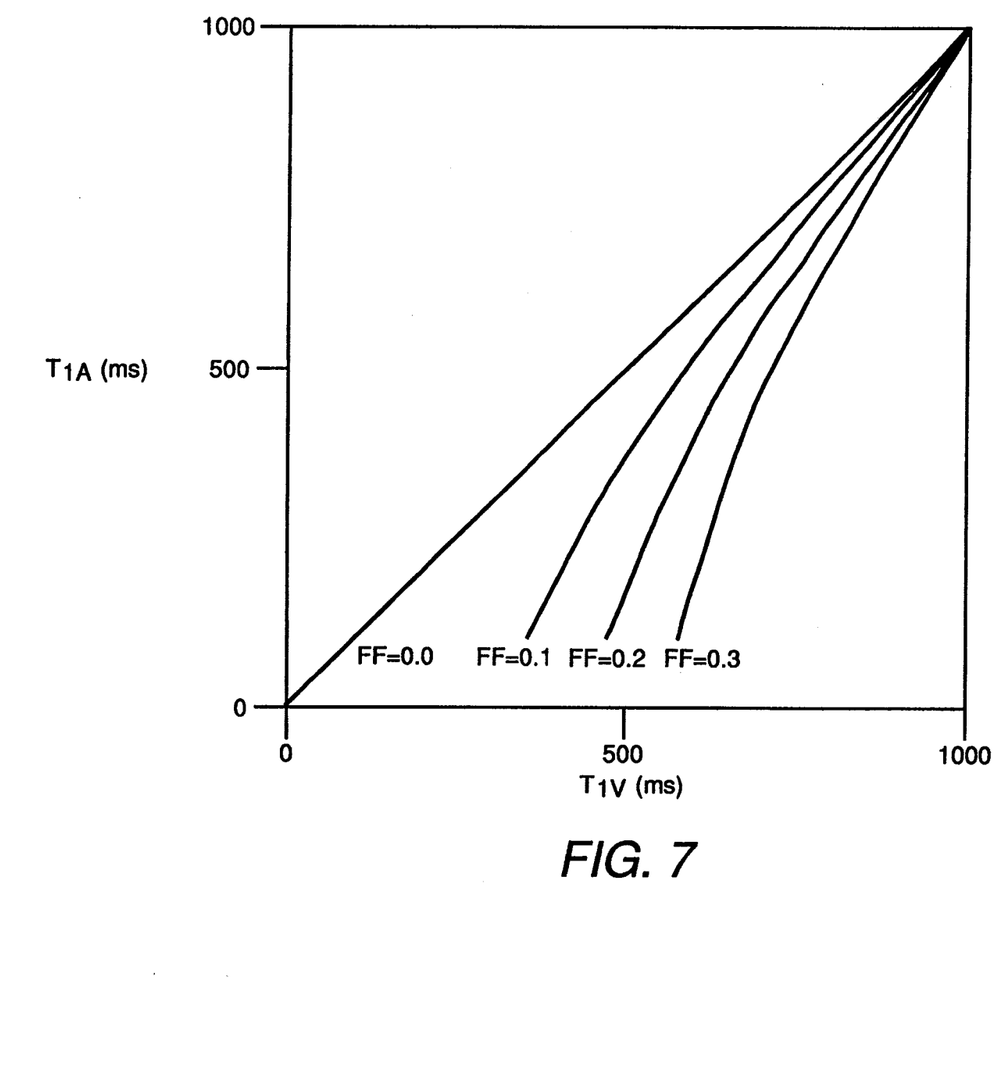
FIG. 7 is a diagram illustrating the relationship between the $T_1$ of blood in the renal arteries and veins for selected filtration fractions.

FIG. 7 illustrates the relationship between $T_{1A}$ and $T_{1V}$ for Filtration Fractions of 0.0, 0.1, 0.2 and 0.3. Note that if the Filtration Fraction is zero, the $T_1$ of blood passing into the kidney is identical to the $T_1$ of blood exiting the kidney since no $T_1$ relaxation contrast agent is removed. For higher values of Filtration Fraction, the concentration of the $T_1$ relaxation contrast agent in the venous renal blood is lower than that found in the arterial blood. Consequently, the $T_1$ of venous blood is longer.

Once the Filtration Fraction has been measured, the Glomerular Filtration Rate, $rate_{GF}$, can be determined from the expression:

$$rate_{GF} = FF * flow_{RB} * (1 - Hct) \quad [6]$$

where $flow_{RB}$ is the Renal Blood Flow and Hct is the hematocrit, or fraction of the blood which is comprised of red blood cells.

Figure 8:
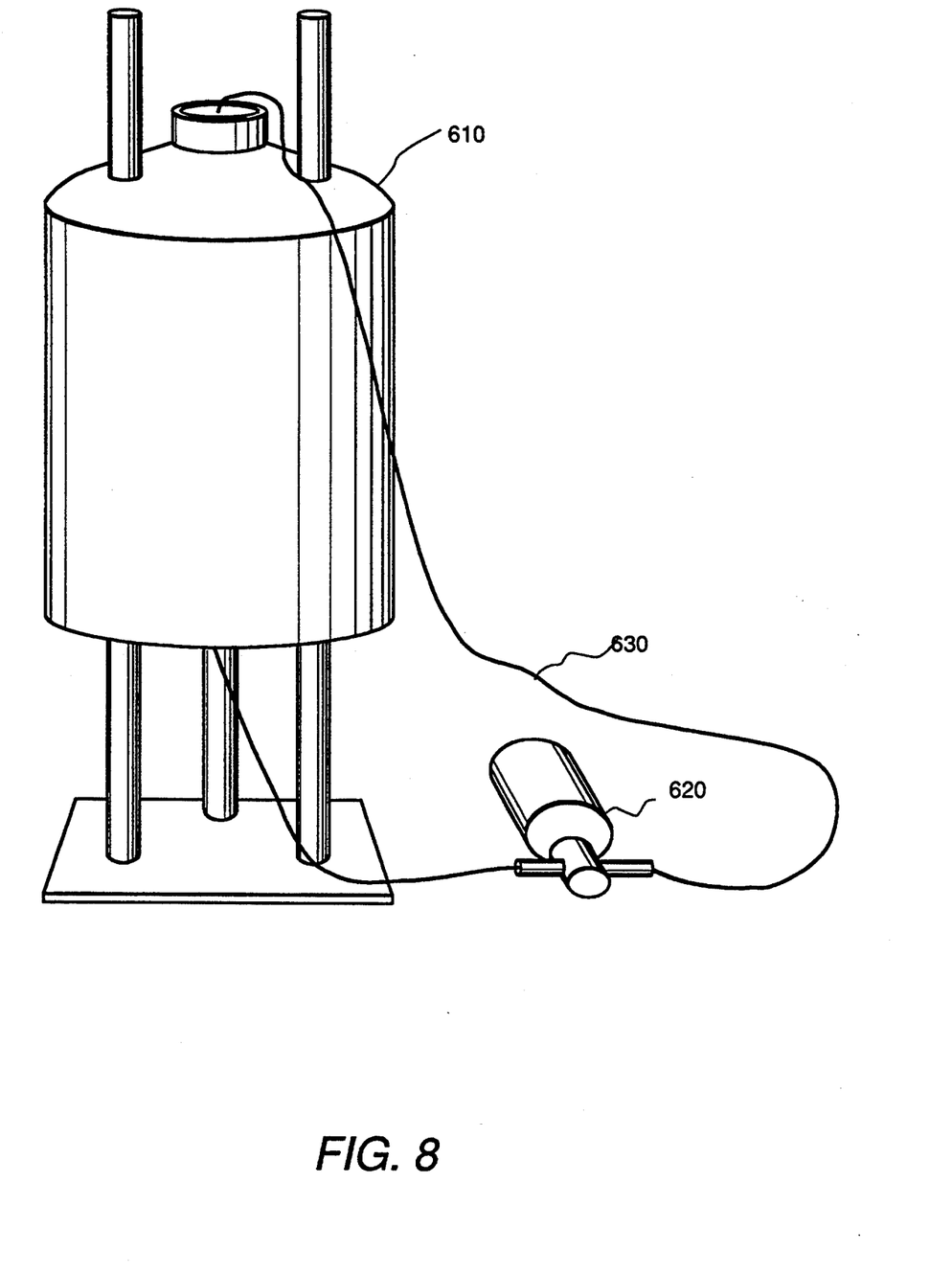
FIG. 8 is perspective view of an alternative embodiment of the invention in which the $T_1$ of a sample solution is determined with a high-resolution nuclear magnetic resonance spectroscopy system.

FIG. 8 shows an alternative embodiment of the present invention in which a high resolution Nuclear Magnetic Resonance (NMR) system is used to obtain NMR spectra. Here a sample solution is circulated through a magnet 610 via connecting tube 630. A pump means 620 is used to move the sample solution through the detection plane created by slice selection magnetic field gradient pulse 140 and detection RF pulse 130 (FIG. 3). Phase-encoding gradient pulse 160, readout dephasing gradient pulse 170 and readout gradient pulse 180 (FIG. 3) can be omitted to permit the detection of an NMR spectrum rather than an MR image. Alternatively, other pulse sequences known in the art of NMR spectroscopy can be employed if desired.

Reduction to Practice

Figure 9:
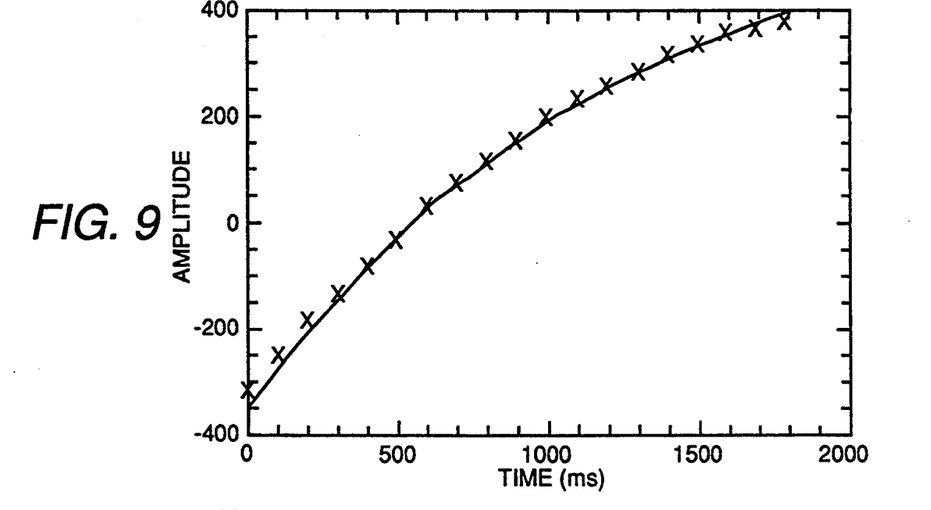
FIG. 9 is the $T_1$ recovery curve for blood prior to the injection of a relaxation contrast agent.
Figure 10:
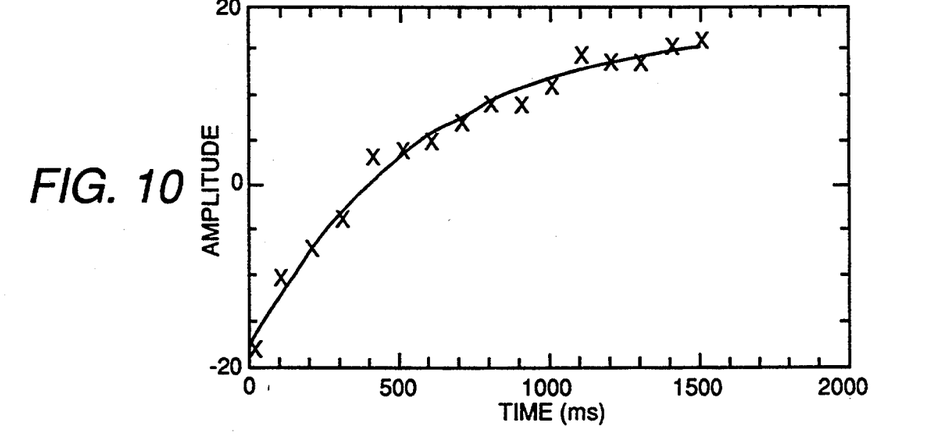
FIG. 10 is the $T_1$ recovery curve for blood in a renal artery after the injection of a relaxation contrast agent.
Figure 11:
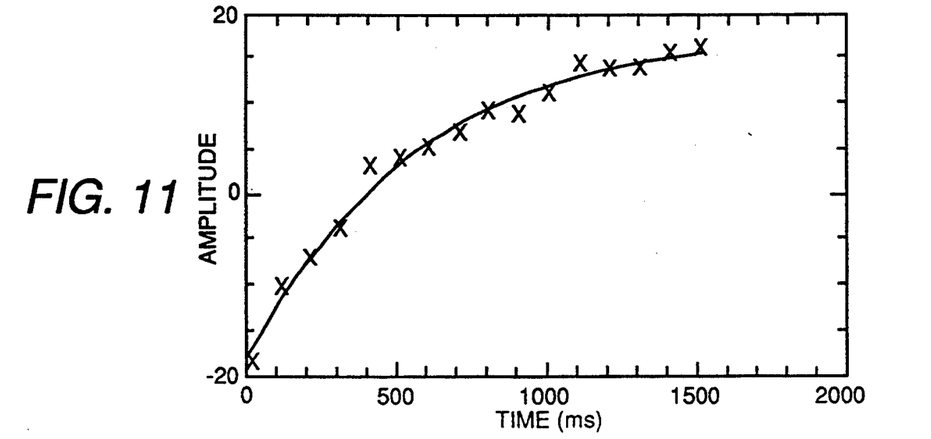
FIG. 11 is the $T_1$ recovery curve for blood in a renal vein after the injection of a relaxation contrast agent.

The present invention has been reduced to practice. FIG. 9 is a graph of a $T_1$ recovery curve of signal intensity measured in the renal artery of a healthy human subject prior to the injection of a $T_1$ relaxation contrast agent. FIG. 10 is a graph of a $T_1$ recovery curve of signal intensity measured in the renal artery after the injection of a $T_1$ relaxation contrast agent (Gd-DTPA). FIG. 11 is a graph of a $T_1$ recovery curve of signal intensity measured in the renal vein after the injection of the $T_1$ relaxation contrast agent. The $T_1$ of blood prior to the $T_1$ relaxation contrast agent injection was measured to be 1229 ms. After injection, the $T_1$ of arterial blood was found to be 568 ms while the $T_1$ of venous blood was found to be 823 ms. These relaxation times were entered into equation [5] to obtain a filtration fraction equal to 0.26. This filtration fraction is well within the expected value for a healthy individual.

While several presently preferred embodiments of the novel $T_1$ measurement system have been described in detail herein, many modifications and variations will now become apparent to those skilled in the art. It is, therefore, to be understood that the appended claims are intended to cover all such modifications and variations as far within the true spirit of the invention.

What is claimed is:

1. A method of measuring renal function in a living subject comprising the steps of:
   a) obtaining a longitudinal spin relaxation time of said subject's blood without any added contrast agents, $T_{1B}$;
   b) injecting a longitudinal spin relaxation time contrast agent into said subject's blood shortening the longitudinal spin relaxation time of said blood;
   c) measuring a longitudinal spin relaxation time of pre-filtered blood, $T_{1A}$, prefiltered blood being blood on its way into the kidney, with magnetic resonance (MR) techniques, subsequent to injecting the contrast agent;
   d) measuring a longitudinal spin relaxation time of post-filtered blood, $T_{1V}$, post-filtered blood being blood on its way out of the kidney, with magnetic resonance (MR) techniques, subsequent to injecting the contrast agent; and
   e) calculating a filtration fraction, FF, from $T_{1A}$, $T_{1B}$, and $T_{1V}$ indicating the fraction of contrast agent filtered from said subject's blood.

2. The method of measuring renal function of claim 1 further comprising the steps of:
   a) obtaining a hematocrit of said subject's blood, Hct;
   b) obtaining a measure of blood flow through said subject's kidney, flow$_{RB}$; and
   c) calculating the glomerular filtration rate from the calculated filtration fraction, the hematocrit and the blood flow through said subject's kidney.

3. The method of claim 2 wherein the glomerular filtration rate rate$_{GL}$ is calculated from filtration fraction, FF, the renal blood flow, flow$_{RB}$, and the hematocrit, Hct according to:

$$rate_{GF} = FF * flow_{RB} * (1 - Hct).$$

4. The method of claim 1 wherein the filtration fraction, FF, is determined according to:

$$FF = \frac{T_{1V} - T_{1A}}{T_{1B} - T_{1A}} * \left[ \frac{T_{1V}}{T_{1B}} \right].$$

* * * * *